(12) United States Patent
Riechers et al.

(10) Patent No.: US 6,627,756 B1
(45) Date of Patent: Sep. 30, 2003

(54) PREPARATION OF PURE TRIETHYLENEDIAMINE

(75) Inventors: Hartmut Riechers, Neustadt (DE); Arthur Höhn, Kirchheim (DE); Joachim Simon, Mannheim (DE); Ortmund Lang, Ohmbach (DE); Hartmut Schoenmakers, Heidelberg (DE); Matthias Rauls, Limburgerhof (DE); Koen Claerbout, Verrebroek (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 34 days.

(21) Appl. No.: 09/613,718

(22) Filed: Jul. 11, 2000

(30) Foreign Application Priority Data

Jul. 23, 1999 (DE) .......................... 199 33 850
Dec. 22, 1999 (DE) .......................... 199 62 455

(51) Int. Cl.⁷ ............................................ C07D 487/08
(52) U.S. Cl. ...................................... 544/352
(58) Field of Search ......................... 544/352

(56) References Cited

U.S. PATENT DOCUMENTS

| | | | | |
|---|---|---|---|---|
| 2,937,176 A | | 5/1960 | Herrick ...................... | 260/268 |
| 3,123,607 A | | 3/1964 | Farkas et al. ................ | 260/268 |
| 3,297,701 A | | 1/1967 | Brader et al. ................ | 260/268 |
| 3,993,651 A | | 11/1976 | Keating ....................... | 260/268 |
| 4,017,494 A | | 4/1977 | Bosche et al. .............. | 260/268 |
| 4,182,864 A | | 1/1980 | Nieh et al. ................... | 544/352 |
| 4,216,323 A | | 8/1980 | Otsuki et al. ................ | 544/352 |
| 4,233,447 A | | 11/1980 | Nieh et al. ................... | 544/352 |
| 4,289,881 A | * | 9/1981 | Imre et al. ................... | 544/352 |
| 4,757,143 A | | 7/1988 | Vanderpool et al. ......... | 544/352 |
| 4,804,758 A | | 2/1989 | Hoelderich et al. ......... | 544/352 |
| 5,741,906 A | | 4/1998 | Santiesteban et al. ....... | 544/352 |
| 2002/0156278 A1 | * | 10/2002 | Lang et al. .................. | 544/352 |

FOREIGN PATENT DOCUMENTS

| | | |
|---|---|---|
| DE | 1 745 627 | 5/1970 |
| DE | 24 42 929 | 3/1976 |
| DE | 26 11 069 | 9/1976 |
| DE | 28 49 993 | 5/1979 |
| DE | 37 18 395 | 12/1987 |
| DE | 36 34 258 | 4/1988 |
| EP | 111 928 | 6/1984 |
| EP | 382 055 | 8/1990 |
| EP | 842 935 A1 | 5/1998 |
| GB | 902073 | 7/1962 |
| GB | 2 080 283 | 2/1982 |
| JP | 49-048609 | 5/1974 |
| JP | 62240674 | 10/1987 |

OTHER PUBLICATIONS

U.S. patent application Ser. No. 10/033,915, Lang et al., filed Jan. 3, 2002.

* cited by examiner

*Primary Examiner*—Mukund J. Shah
*Assistant Examiner*—Thomas McKenzie
(74) *Attorney, Agent, or Firm*—Keil & Weinkauf

(57) ABSTRACT

Pure triethylenediamine (TEDA) is prepared by vaporizing TEDA, introducing the gaseous TEDA into a liquid solvent and subsequently crystallizing the TEDA from the solution obtained in this way.

9 Claims, No Drawings

PREPARATION OF PURE TRIETHYLENEDIAMINE

The present invention relates to a process for preparing pure triethylenediamine (=TEDA=DABCO®=1,4-diazabicyclo[2.2.2]octane) and solutions thereof.

Triethylenediamine (TEDA), which is a solid under standard conditions, is an important catalyst for the production of polyurethane foams.

For this and other applications, a pure, virtually odorless and pure white TEDA which has as little discoloration as possible, e.g. has a very low APHA color number (DIN-ISO 6271), and retains these properties even after prolonged storage (for, for example, 6, 12 or more months) is desired.

Various processes for preparing and purifying TEDA are known:

DT-A-24 42 929 relates to a process for preparing TEDA by elimination of glycol from N,N'-di(hydroxyethyl)piperazine in the presence of $Al_2O_3$ as catalyst.

U.S. Pat. No. 3,297,701 discloses a process for preparing diazabicyclo[2.2.2]octanes by reaction of corresponding hydroxyethylpiperazines or aminoethylpiperazines at elevated temperature in the presence of metal phosphates, e.g. calcium phosphate.

DE-A-36 34 258 describes a process for preparing diazabicyclo[2.2.2]octanes by reaction of corresponding hydroxyethylpiperazines or aminoethylpiperazines in the presence of zirconium phosphates.

DE-A-1 745 627 relates to a process for preparing TEDA and piperazine by reaction of ethylenediamine over an acid silica-alumina catalyst at elevated temperature and isolation of the TEDA by distillation and/or crystallization.

DE-A-37 18 395 describes the preparation of TEDA by reaction of an acyclic hydroxyethylethylenepolyamine and/or cyclic hydroxyethylethylenepolyamine in the presence of a phosphorus-containing titanium dioxide or zirconium dioxide catalyst.

EP-A-111 928 describes the use of particular phosphate catalysts, e.g. monophosphates or pyrophosphates of magnesium, calcium, barium or aluminum, in organic condensation reactions, e.g. the conversion of N-(2-hydroxyethyl)piperazine into TEDA.

EP-A-382 055 discloses a process for preparing TEDA, in which 1,2-diaminoethane and from 0 to 200 mol % of piperazine are reacted over aluminum silicate, boron silicate, gallium silicate and/or iron silicate zeolites at elevated temperatures.

EP-A-842 935 describes a process for preparing TEDA by reaction of an amine compound such as monoethanolamine over a catalyst to give a product comprising TEDA and piperazine and subsequent reaction of this product with an ethylating compound containing at least one N and/or O atom in the presence of a shape-selective zeolite catalyst.

U.S. Pat. No. 5,741,906 relates to the preparation of TEDA by reaction of an amine compound such as monoethanolamine over a zeolite catalyst of the pentasil type.

The known processes for preparing TEDA lead to the formation of crude reaction products comprising not only TEDA but also water, by-products, e.g. piperazine and high molecular weight polymers, and possibly a solvent used in the reaction. TEDA is usually separated from these mixtures by batchwise or continuous distillation or rectification and is normally purified in a subsequent step by crystallization or recrystallization.

Owing to its properties [hygroscopic, temperature-sensitive, boiling point (174° C. at atmospheric pressure) and melting point (158–160° C.) are close to one another], TEDA can be handled only with difficulty and with an appropriate engineering outlay if deterioration in the quality of the TEDA in respect of color, color stability (undesirable increase in the color number, e.g. measured as APHA color number, over the storage time), odor (undesirable odor due to cyclic saturated 5-membered ring N-heterocycles or other cyclic saturated 6-membered ring N-heterocycles and/or aromatic 5- or 6-membered ring N-heterocycles) and purity is to be avoided.

The TEDA obtained by the known processes after distillation or rectification and solutions prepared therefrom is/are usually not commercially acceptable due to the color (e.g. measured as APHA color number), color stability and/or odor and the quality of the TEDA can only be improved by further purification steps, for example technically complicated crystallization or recrystallization.

There has therefore been no lack of attempts to discover alternative processes for preparing TEDA of improved quality.

DT-A-26 11 069 relates to: the isolation of TEDA, in which propylene glycol is added to the crude TEDA and the mixture is subsequently fractionally distilled.

DE-A-28 49 993 discloses a process for separating off and isolating TEDA, in which water is added to the crude TEDA and the mixture is subsequently distilled.

JP-A-49 048 609 claims a process for purifying piperazine and/or TEDA by fractional distillation of a mixture comprising piperazine and/or TEDA. This process comprises dissolution of the piperazine and/or TEDA distillates in water or an organic solvent, where the solvent can be in liquid or gaseous form, and collection of the solutions of the distillates. According to this patent application, this.process is said to achieve the object of preventing blockages caused by solids in the distillation apparatus. The description, the schematic depiction of the distillation apparatus and the examples in this patent application teach that, for this purpose, the piperazine or the TEDA is firstly liquefied in a condenser at the top of the distillation column and is only then dissolved in the solvent.

A disadvantage of these processes is that they do not give the TEDA in the desired quality.

It is an object of the present invention to find an improved, efficient and economical process for preparing pure triethylenediamine (TEDA) and solutions thereof, which process gives TEDA and TEDA solutions of improved quality in respect of color, color stability, odor and purity.

We have found that this object is achieved by a process for preparing a solution of pure triethylenediamine (TEDA) which comprises vaporizing TEDA and introducing the gaseous TEDA into a liquid solvent. Subsequent crystallization of the TEDA from the solution obtained in this way gives pure TEDA having the improved quality required.

The process of the present invention, in which the introduction of the gaseous TEDA into a liquid solvent will hereinafter also be referred to as the TEDA quench, significantly reduces the formation of undesirable by-products which lead to reduced quality. The presence of liquid TEDA at the outlet of the vaporization or distillation apparatus is avoided according to the present invention by the liquefaction of the distillate customary in distillations not taking place.

Suitable solvents for this TEDA quench are, in particular, cyclic or acyclic (=aliphatic) hydrocarbons, especially branched or unbranched alkanes or alkane mixtures such as n-pentane, isopentane, cyclopentane, hexane, cyclohexane, heptane, octane, petroleum ether), chlorinated aliphatic hydrocarbons (especially chlorinated alkanes such as dichloromethane, trichloromethane, dichloroethane, trichloroethane), aromatic hydrocarbons (for example benzene, toluene, xylenes), chlorinated aromatic hydrocarbons (for example chlorobenzene), alcohols (for example methanol, ethanol, ethylene glycol, 1,4-butanediol and polyether alcohols, especially polyalkylene glycols such as diethylene glycol, dipropylene glycol), ketones, especially aliphatic ketones such as acetone, methyl ethyl ketone, diethyl ketone), aliphatic carboxylic esters (for example methyl acetate, ethyl acetate), aliphatic nitriles (for example acetonitrile, propionitrile), ethers (for example dioxane, THF, diethyl ether, ethylene glycol dimethyl ether) and mixtures thereof.

In the preparation according to the present invention of a solution of pure TEDA which can, for example, be used as catalyst solution in the production of polyurethane foam, the solvent used for the TEDA quench is preferably an alcohol (e.g. ethylene glycol, 1,4-butanediol, dipropylene glycol). The color number of a 33% strength by weight TEDA solution in dipropylene glycol obtained in this way is less than 150 APHA, in particular less than 100 APHA.

In the preparation according to the present invention of pure (crystalline) TEDA, the solvent used for the TEDA quench is preferably an aliphatic hydrocarbon, in particular a saturated aliphatic hydrocarbon having from 5 to 8 carbon atoms (for example pentane, hexane, heptane). The crystallization of the pure TEDA from the TEDA solution prepared according to the present invention can be carried out by methods known to those skilled in the art. The TEDA crystals obtained by means of a subsequent multistage or preferably single-stage crystallization are highly pure (purity generally at least 99.5% by weight, in particular at least 99.9% by weight) and the color number of a 33% strength by weight solution in dipropylene glycol is less than 50 APHA, in particular less than 30 APHA.

The introduction according to the present invention of the gaseous TEDA into the liquid solvent is carried out in a quenching apparatus, e.g. preferably in a falling film condenser (thin film, trickle film or falling stream condenser) or in a nozzle apparatus. Here, the gaseous TEDA can be conveyed in cocurrent or in countercurrent to the liquid solvent. The gaseous TEDA is, advantageously introduced into the quenching apparatus from the top. Also advantageous is tangential introduction of the liquid solvent at the top of the falling film condenser or introduction of the liquid solvent through one or more nozzles so as to achieve complete wetting of the inner wall of the quenching apparatus.

The solvent can be passed once through the apparatus or can be circulated.

The amount of solvent used is not critical to the present invention and is selected from points of view of convenience, effectiveness and cost. In general, the quench is operated so as to give, depending on the type of solvent, solutions having a TEDA content of from about 1 to 50% by weight, preferably from 20 to 40% by weight.

In general, the temperature in the TEDA quench is set to from 20 to 100° C., preferably from 30 to 60° C., by heating/cooling the solvent used and/or the quenching apparatus. The absolute pressure in the TEDA quench is generally from 0.5 to 1.5 bar.

Owing to the partial vaporization of the solvent used as a result of the heat introduced by the gaseous TEDA, the gas space in the quenching apparatus is saturated with solvent vapor. This significantly reduces or completely prevents desublimation of the gaseous TEDA and the consequent blockage problems caused by deposition of solids in the discharge lines.

The TEDA to be vaporized in the process of the present invention can be obtained by known methods, e.g. by reaction of monoethanolamine, diethanolamine, triethanolamine, ethylenediamine, diethylenetriamine, triethylenetetramine, piperazine, N-(2-hydroxyethyl)piperazine, N,N'-bis(2-hydroxyethyl)piperazine, N-(2-aminoethyl)piperazine, N,N'-bis(2-aminoethyl)piperazine, morpholine or mixtures thereof over a catalyst [e.g. metal pyrophosphates, metal phosphates (such as alkaline earth metal monohydrogenphosphates), zeolites, zirconium phosphates, $Al_2O_3$, $SiO_2$, phosphorus-containing $TiO_2$ or $ZrO_2$] at elevated temperature (generally from 250 to 450° C.). The pressure here is usually from 0.1 to 50 bar, in particular from 0.1 to 5 bar. If desired, the reaction can be carried out in the presence of an inert polar aprotic solvent (e.g. N-alkylpyrrolidone (such as N-methylpyrrolidone), dioxane, THF, dialkylformamide (such as dimethylformamide), dialkylacetamide (such as dimethylacetamide)) and an inert carrier gas (e.g. $N_2$ or Ar).

The resulting TEDA can be purified by distillation and/or crystallization.

Such processes are described, for example, in DT-A-24 42 929, U.S. Pat. No. 3,297,701, DE-A-36 34 258, DE-A-1 745 627, DE-A-37 18 395, EP-A-111 928, EP-A-382 055, EP-A-842 935, EP-A-842 936, EP-A-831 096, EP-A-952 152 and U.S. Pat. No. 5,741,906.

The TEDA which does not meet quality requirements in respect of color, color stability, odor and/or purity and is to be used as starting material in the process of the present invention can be vaporized by methods and under conditions known to those skilled in the art, e.g. in a distillation apparatus which is charged/supplied with the TEDA or a mixture comprising the TEDA (crude TEDA). The gaseous TEDA is preferably obtained at the top or at a side offtake of a distillation column. The gaseous TEDA used in the process of the present invention generally has a purity of greater than 90% by weight, preferably greater than 95% by weight, in particular greater than 97% by weight.

The time interval between the time at which the gaseous TEDA used in the process of the present invention is obtained and the time at which the TEDA quench is carried out is advantageously $\leq 10$ seconds.

In a preferred embodiment, the process of the present invention can be carried out as follows:

A mixture comprising the TEDA to be vaporized, which has been obtained, for example, in a continuous process by reaction of N-(2-hydroxyethyl)piperazine in a gas-phase reactor at from 320 to 420° C. and from 0.5 to 1.5 bar in the presence of a polar aprotic solvent (e.g. N-alkylpyrrolidone (such as N-methylpyrrolidone), dioxane, THF, dialkylformamide (such as dimethylformamide), dialkylacetamide (such as dimethylacetamide)), a carrier gas (e.g. $N_2$ or Ar) and an alkaline earth metal monohydrogenphosphate as catalyst, is introduced into a distillation apparatus with a distillation column having, for example, about 30 theoretical plates. Here, low boilers (e.g. water, piperazine, N-ethylpiperazine) are separated off via the top at a temperature at the top of from 100° C. to 120° C. and a pressure of generally from 500 mbar to 1.5 bar.

The bottoms are pumped to a further distillation column having, for example, about 25 theoretical plates. In this column, operated at a pressure of generally from 500 mbar to 1.5 bar, any solvent used in the synthesis of TEDA is separated off via the side offtake and may, if desired, be returned to the synthesis reactor and the high boilers are discharged via the bottom outlet. TEDA having a purity of greater than 95% by weight, in particular greater than 97% by weight, is taken off in vapor form at the top of the column via a partial condenser and is cooled suddenly and simultaneously dissolved in a solvent (e.g. pentane, dipropylene glycol) at generally from 30 to 100° C., preferably from 30 to 60° C., in a falling film condenser (TEDA quench).

EXAMPLES

Example 1

The experiments were carried out in a 4 l (catalyst volume) salt bath reactor (shell-and-tube containing 7 tubes, internal diameter 21 mm, length 2 m) made of stainless steel and heated by means of electric heating tapes. The lines for the reactor feed, reactor output and the distillation section were partly configured as double-wall tubes and heated by means of oil. The plant components were protectively heated and were individually brought to the temperature required in each case by use of various heating circuits.

The catalyst used was $CaHPO_4$ in the form of pellets (diameter about 3 mm, height about 3 mm) (catalyst bed).

The catalyst was produced as follows:

$CaHPO_4 \times 2\ H_2O$ was heated at about 250° C. for 16 hours in a drying oven equipped with a ventilation facility. 2% by weight of graphite was subsequently mixed into the powder obtained and the resultant powder mixture was pressed at 270 bar by means of an extruder to give pellets.

1600 g/h of the feed and 150 standard l/h (standard l=standard liters=volume at STP) of nitrogen were passed at atmospheric pressure through the salt bath reactor heated to 380° C. (weight hourly velocity over the catalyst: 0.4 kg of feed per l of cat. (bed volume) and per h).

The feed had the following composition (figures in % by weight).

| | |
|---|---|
| N-(2-hydroxyethyl)piperazine | 33% |
| N,N'-di(2-hydroxyethyl)piperazine | 12% |
| Piperazine | 15% |
| N-methylpyrrolidone | 19% (as solvent) |
| Water | 21% |

The gaseous reaction product was condensed at 60° C. in a quench using a circulated liquid which comprised previously obtained liquid reaction product (see below) (=reaction product quench).

Analysis of the condensate indicated the following composition (figures in % by weight):

| | |
|---|---|
| Piperazine | 7% |
| Ethylpiperazine | 3% |
| Triethylenediamine (TEDA) | 29% |
| N-methylpyrrolidone | 23% |
| Water | 27% |
| Remainder | high boilers and other by-products |

The uncondensed components were, after a gas/liquid separator, discharged via a cold trap and a subsequent wash bottle.

Part of the liquid reaction product was cooled and used as circulated liquid (for the reaction product quench), while another part was continuously pumped via a pump to a distillation column (K 1). The glass column had a diameter of 50 mm and was equipped with 60 bubble cap trays. The reflux ratio was about 1.4:1. The low boilers (water, piperazine, ethylpiperazine) were taken off in liquid form at the top of the column at atmospheric pressure and a temperature at the top of 116° C.

Analysis of the low boiler fraction indicated the following composition (figures in % by weight):

| | |
|---|---|
| Piperazine | 17% |
| Ethylpiperazine | 9% |
| Triethylenediamine (TEDA) | 2% |
| Water | 63% |
| Remainder | By-products |

The bottoms from the distillation column were pumped continuously at 184° C. to a subsequent distillation column K 2. The glass column K 2 had a diameter of 50 mm and was equipped with 50 bubble cap trays. The reflux ratio was about 10:1. The N-methylpyrrolidone solvent was taken off at a temperature of 208° C. from a side offtake above the 1st bubble cap tray and was recirculated to the reactor, while the high boilers were discharged at 225° C. at the bottom of the column. TEDA was taken off in vapor form at the top of the column and cooled suddenly and simultaneously dissolved at about 30° C. in the liquid solvent pentane (mixture of 80% by weight of n-pentane and 20% by weight of isopentane) (=TEDA quench). The TEDA quench was carried out using a falling film condenser (trickle film or falling stream condenser) in which gaseous TEDA was introduced at the top. The pentane was introduced tangentially at the top of the falling film condenser. The resulting solution had the following composition (figures in % by weight):

| | |
|---|---|
| Piperazine | 0.02% |
| Ethylpiperazine | 0.02% |
| Triethylenediamine (TEDA) | 7.5% |
| N-methylpyrrolidone | 0.01% |
| Pentane | 92% |

After the pentane had been separated off by cooling crystallization at 0° C. under nitrogen, TEDA was obtained in a purity of at least 99.5% by weight.

A 33% strength by weight solution of the resulting TEDA in dipropylene glycol (DPG) had an APHA color number of 28.

The TEDA obtained did not smell of cyclic saturated 5-membered ring N-heterocycles or other cyclic saturated 6-membered ring N-heterocycles and/or aromatic 5- or 6-membered ring N-heterocycles.

Example 2

When the procedure of Example 1 was repeated using dipropylene glycol (DPG) in place of pentane as solvent for the TEDA quench and without subsequent crystallization of the TEDA from the solvent, the following result was obtained.

Composition of the TEDA/DPG solution (figures in % by weight):

| | |
|---|---|
| Piperazine | 0.03% |
| Ethylpiperazine | 0.06% |
| Triethylenediamine (TEDA) | 25% |
| N-methylpyrrolidone | 0.01% |
| Dipropylene glycol | 73% |

This TEDA/DPG solution had an APHA color number of 140 and can be used directly as catalyst in the production of polyurethanes.

The TEDA/DPG solution obtained did not smell of cyclic saturated 5-membered ring N-heterocycles or other cyclic saturated 6-membered ring N-heterocycles and/or aromatic 5- or 6-membered ring N-heterocycles.

Comparative Example

When the procedure of Example 1 was repeated with TEDA being taken off in liquid form at the top of the glass column K 2 and no TEDA quench being carried out, the following result was obtained.

Composition of the distillate (figures in % by weight):

| | |
|---|---|
| Piperazine | 0.07% |
| Ethylpiperazine | 0.06% |
| Triethylenediamine (TEDA) | 98.8% |
| N-Methylpyrrolidone | 0.01% |

Condensation of TEDA in a condenser by conventional means and conveying the liquid TEDA further at the necessary high temperatures (>160° C.), e.g. to the distillation unit, leads to considerable thermal stressing of the TEDA and to formation of undesirable decomposition products.

In terms of its color and its odor, the TEDA obtained in this way had unsatisfactory properties and was therefore not commercially acceptable:

APHA color number of a 33% strength by weight solution in dipropylene glycol (DPG): 1000, Odor of cyclic saturated 5-membered ring N-heterocycles or other cyclic saturated 6-membered ring N-heterocycles and/or aromatic 5- or 6-membered ring N-heterocycles.

A layer crystallization of the TEDA obtained as a further purification step was not able to effect a significant improvement in the TEDA quality in respect of the odor:

APHA color number of a 33% strength by weight solution in dipropylene glycol (DPG): 130, Odor of cyclic saturated 5-membered ring N-heterocycles or other cyclic saturated 6-membered ring N-heterocycles and/or aromatic 5- or 6-membered ring N-heterocycles.

We claim:

1. A process for preparing a solution of pure triethylenediamine (TEDA), which comprises vaporizing TEDA and introducing the gaseous TEDA into a liquid solvent.

2. A process as claimed in claim 1, wherein the gaseous TEDA is obtained at the top or at a side offtake of a distillation column.

3. A process for preparing pure triethylenediamine (TEDA), which comprises preparing a solution of pure TEDA as claimed in claim 1 and subsequently crystallizing the TEDA from this solution.

4. A process as claimed in any of claim 1, wherein the liquid solvent is selected from the group consisting of cyclic or acyclic hydrocarbons, chlorinated aliphatic hydrocarbons, aromatic hydrocarbons, alcohols, ketones, aliphatic carboxylic esters, aliphatic nitriles and ethers.

5. A process as claimed in claim 1, wherein the liquid solvent used is pentane or dipropylene glycol.

6. A process as claimed in claim 1, wherein the gaseous TEDA to be introduced into the liquid solvent has a purity of greater than 95% by weight.

7. A process as claimed in claim 1, wherein the TEDA to be vaporized has been obtained by reaction of monoethanolamine, diethanolamine, triethanolamine, ethylenediamine, diethylenetriamine, triethylenetetramine, piperazine, N-(2-hydroxyethyl)piperazine, N,N'-bis(2-hydroxyethyl)piperazine, N-(2-aminoethyl)piperazine, N,N'-bis(2-aminoethyl)piperazine, morpholine or a mixture thereof over a catalyst at elevated temperature.

8. A process as claimed in claim 7, wherein the catalyst is a metal phosphate or a zeolite.

9. A process as claimed in claim 7, wherein the reaction has been carried out at from 250 to 450° C. in the gas phase.

* * * * *